(12) United States Patent
Wang et al.

(10) Patent No.: US 8,354,512 B2
(45) Date of Patent: Jan. 15, 2013

(54) LIGAND AND METAL COMPLEX

(75) Inventors: Yun-Ming Wang, Hsinchu (TW);
Ting-Jung Chen, Yongkang (TW)

(73) Assignee: National Chiao Tung University, Hsinchu (TW)

( * ) Notice: Subject to any disclaimer, the term of this patent is extended or adjusted under 35 U.S.C. 154(b) by 287 days.

(21) Appl. No.: 12/658,332

(22) Filed: Feb. 8, 2010

(65) Prior Publication Data

US 2011/0065905 A1 Mar. 17, 2011

(30) Foreign Application Priority Data

Sep. 16, 2009 (TW) ................ 98131213 A

(51) Int. Cl.
*A61K 51/04* (2006.01)
(52) U.S. Cl. ....... 534/10; 424/1.11; 424/1.65; 424/1.69; 534/11; 534/14; 534/15
(58) Field of Classification Search ........... 424/1.11, 424/1.49, 1.65, 1.69, 1.73; 514/1, 1.11; 530/300, 530/316, 317, 329, 331; 534/7, 10–16
See application file for complete search history.

(56) References Cited

OTHER PUBLICATIONS

Wang, Yun-Ming, et al., "Synthesis and complexation of Gd3+, Ca2+, Cu2+ and Zn2+ by 3,6,10-tri (carboxymethyl)-3,6,10-triazadodecanedioic acid"; J. Chem. Soc., Dalton Trans., 1998; pp. 4113-4118.
Cheng, Tsan-Hwang, et al., "Thermodynamic Stability and Physicochemical Characterization of Ligand (4S)-4-Benzyl-3,6,10-tris(carboxymethyl)-3,6,10-triazadodecanedioic Acid (H5[(S)-4-Bz-ttda]) and Its Complexes Formed with Lanthanides, Calcium(II), Zinc(II), and Copper(II) Ions"; Helvetica Chimica Acta—vol. 85 (2002); pp. 1033-1050.
Caravan, Peter, et al., "Gadolinium(III) Chelates as MRI Contrast Agents: Structure, Dynamics, and Applications"; American Chemical Society (1999); pp. 2293-2352.
Uggeri, Fulvio, et al., "Novel Contrast Agents for Magnetic Resonance Imaging. Synthesis and characterization of the Ligand BOPTA and Its Ln(III) Complexes (Ln = Gd, La, Lu). X-ray Structure of Disodium (TPS-9-145337286-C-S)-[4-Carboxy-5,8,11-tris(carboxymethyl)-1-phenyl-2-oxa-5,8,11-triazatridecan-13-0ato(5−) in a Mixture with Its Enantiomer"; Inorg. Chem 1995, American Chemical Society (1995), vol. 34; pp. 633-642.
Vander Elst, Luce, et al., "Stereospecific binding of MRI contrast agents to human werum albumin: the case of Gd-(S)-EOB-DTPA (Eovist) and its (R) isomer"; J. Biol. Inorg. Chem (2001), vol. 6; pp. 196-200.

*Primary Examiner* — D L Jones
(74) *Attorney, Agent, or Firm* — Osha Liang LLP

(57) ABSTRACT

A ligand of Formula (I) is provided:

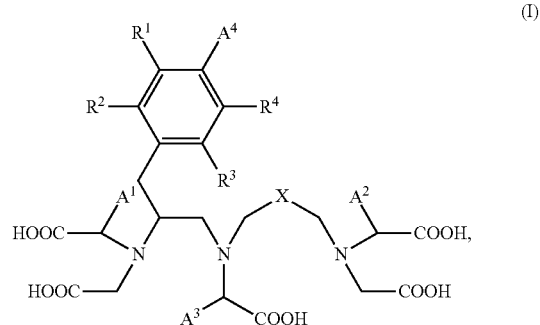

wherein $A^4$ represents a hydrogen atom, a nitro group, an amino group, a thiocyanato group, or —Z—Y, in which Z is a divalent linking group and Y is a group derived from a biocompatible molecule, with the proviso that when X is methylene, $A^4$ cannot be a hydrogen atom or a nitro group. A metal complex having the ligand is also provided and is useful as a blood pool contrast agent or a targeting contrast agent.

18 Claims, 1 Drawing Sheet
(1 of 1 Drawing Sheet(s) Filed in Color)

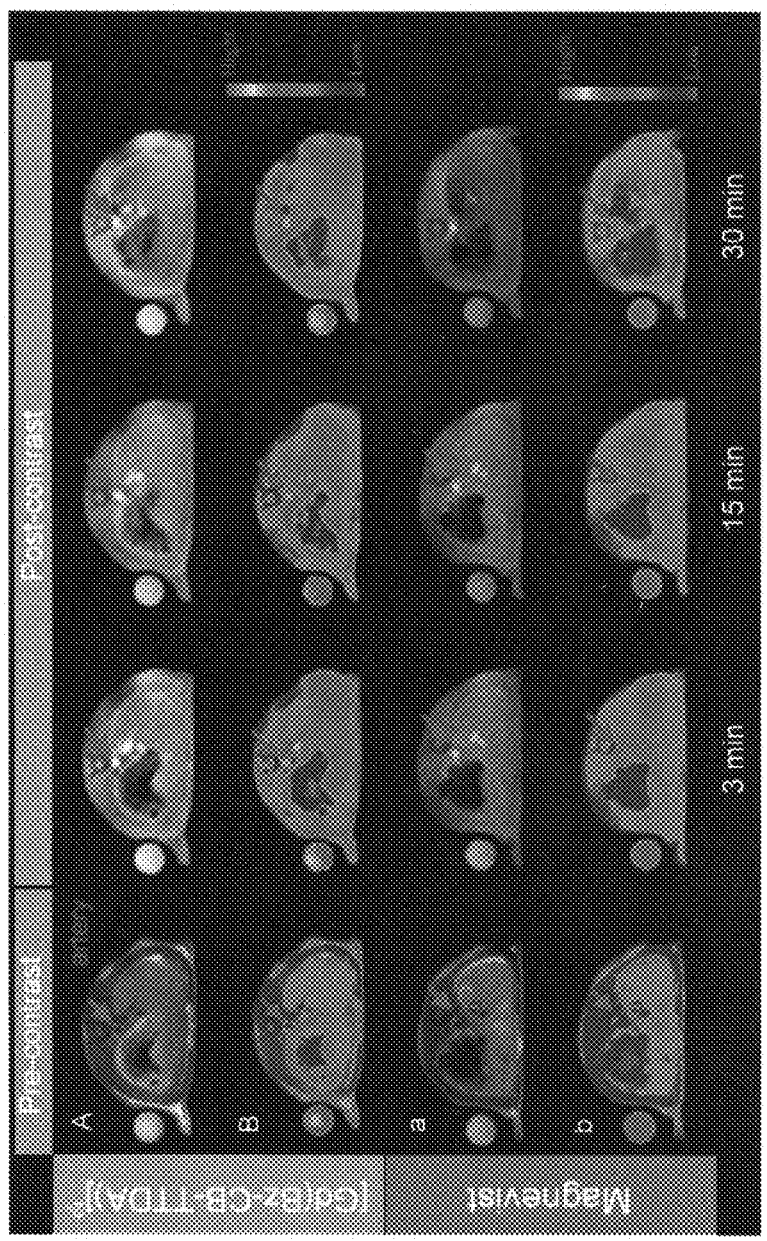

SEQUENCE LISTING

<160> NUMBER OF SEQ ID NOS: 1

<210> SEQ ID NO 1
<211> LENGTH: 6
<212> TYPE: PRT
<213> ORGANISM: artificial sequence
<220> FEATURE:
<223> OTHER INFORMATION: targeting peptide sequence

<400> SEQUENCE: 1

Leu Ala Arg Leu Leu Thr
1               5

LIGAND AND METAL COMPLEX

CROSS-REFERENCE TO RELATED APPLICATION

This application claims priority of Taiwanese Application No. 098131213, filed on Sep. 16, 2009.

BACKGROUND OF THE INVENTION

1. Field of the Invention

This invention relates to a ligand and a metal complex, more particularly to a ligand and a metal complex made from the ligand and useful as a magnetic resonance imaging (MRI) contrast agent, for example a blood pool contrast agent or a targeting contrast agent.

2. Description of the Related Art

MRI is used in in vivo imaging techniques for medical diagnosis. The image signal intensity generated in MRI depends not only on the amount of targeted tissue water, but also on the spin-lattice relaxation time (T1) and the spin-spin relaxation time (T2) of protons of the targeted tissue water. Reduction of T1 leads to an increase in the image signal intensity. Contrast agents are commonly used in MRI for improving image contrast due to their effect on reducing T1.

In Y. M. Wang, et al., *J. Chem. Soc., Dalton Trans*, 1998, pp. 4113-4118, there is disclosed a ligand of 3,6,10-tri-(carboxymethyl)-3,6,10-triazadodecanedioic acid (TTDA). The publication also shows that TTDA exhibits a better effect on reducing T1 than that of diethylene triamine-pentaacetic acid (DTPA).

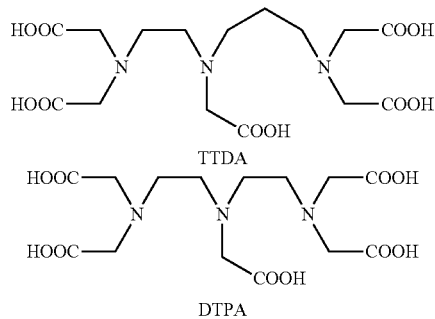

In Y. M. Wang, et al., *Helv. Chim. Acta*, 2002, 85, 1033, there is disclosed a modified TTDA, (S)-4-Bz-TTDA, which has a formula:

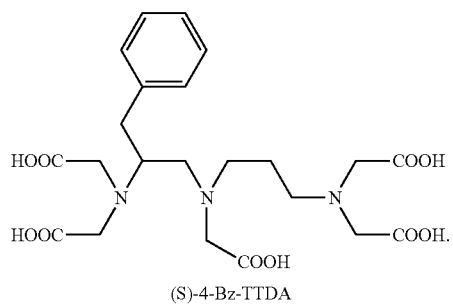 [SMILES: O=C(O)CN(CCCN(CC(=O)O)CC(Cc1ccccc1)N(CC(=O)O)CC(=O)O)CC(=O)O]

Although (S)-4-Bz-TTDA is useful as a hepatobiliary MRI contrast agent, it is not suitable for MRI diagnosis of other targets.

Hence, there is a need to find a contrast agent that has a greater effect on reducing T1 and to develop a contrast agent for MRI diagnosis of various targeted tissues or organs, especially for blood pool contrast agents and targeting contrast agents exhibiting bioactivity.

SUMMARY OF THE INVENTION

Therefore, an object of the present invention is to provide a ligand that exhibits an excellent chelation with a paramagnetic metal ion.

Another object of the present invention is to provide a metal complex having the ligand and a paramagnetic metal ion chelated to the ligand. The metal complex exhibits high stability, high relaxivity and better biocompatibility.

According to one aspect of this invention, there is provided a ligand of Formula (I):

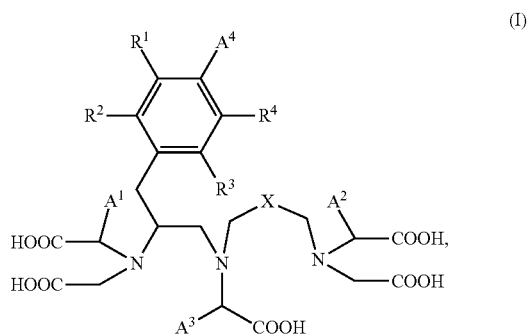

wherein, in Formula (I),

X represents methylene, 1,1-cyclobutylene, 1,1-cyclopentylene, or 1,1-cyclohexylene;

$A^1$, $A^2$ and $A^3$ independently represent a hydrogen atom, a $C_1$~$C_3$ alkyl group, a $C_1$~$C_3$ phenylalkyl group, a $C_1$~$C_3$ methoxyphenylalkyl group, diphenylmethyl or a $C_1$~$C_3$ isothiocyanato phenylalkyl;

$A^4$ represents a hydrogen atom, a nitro group, an amino group, a thiocyanato group, or —Z—Y, in which Z is a divalent linking group and Y is a group derived from a biocompatible molecule, with the proviso that when X is methylene, $A^4$ cannot be a hydrogen atom or a nitro group; and $R^1$, $R^2$, $R^3$, and $R^4$ independently represent a hydrogen atom, an amino group, a nitro group or a thiocyanato group.

According to another aspect of this invention, there is provided a metal complex comprising: a paramagnetic metal ion; and a ligand of Formula (i) chelated with the paramagnetic metal ion:

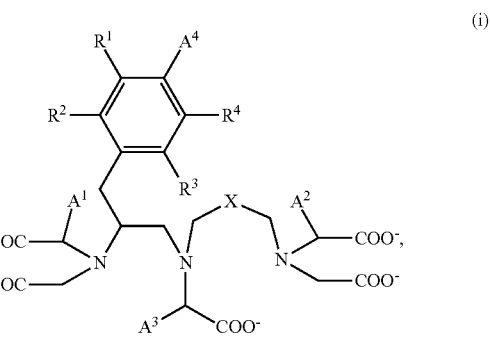

wherein, in Formula (i), X, $A^1$, $A^2$, $A^3$, $A^4$, $R^1$, $R^2$, $R^3$ and $R^4$ have the same definitions as in Formula (I).

BRIEF DESCRIPTION OF THE DRAWING

The patent or application file contains at least one drawing executed in color. Copies of this patent or patent application publication with color drawing(s) will be provided by the Office upon request and payment of the necessary fee.

Other features and advantages of the present invention will become apparent in the following detailed description of the preferred embodiments of this invention, with reference to the accompanying drawing, in which:

FIG. 1 is a picture illustrating the image of in vivo test of the metal complexes [Gd(Bz-CB-TTDA)]$^{2-}$ and Magnevist, in which (A) is an image tested from [Gd(Bz-CB-TTDA)]$^{2-}$ and (a) is an image tested from Magnevist.

DETAILED DESCRIPTION OF THE PREFERRED EMBODIMENTS

This invention provides a ligand of Formula (I):

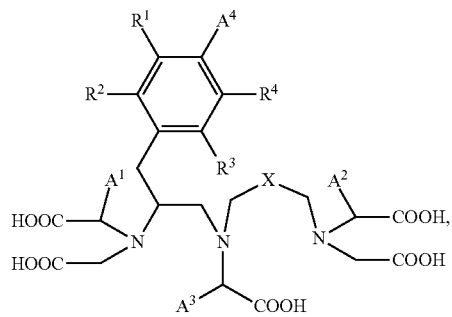

wherein, in Formula (I),

X represents methylene, 1,1-cyclobutylene, 1,1-cyclopentylene, or 1,1-cyclohexylene;

$A^1$, $A^2$ and $A^3$ independently represent a hydrogen atom, a $C_1$~$C_3$ alkyl group, a $C_1$~$C_3$ phenylalkyl group, a $C_1$~$C_3$ methoxyphenylalkyl group, diphenylmethyl or a $C_1$~$C_3$ isothiocyanato phenylalkyl;

$A^4$ represents a hydrogen atom, a nitro group, an amino group, a thiocyanato group, or —Z—Y, in which Z is a divalent linking group and Y is a group derived from a biocompatible molecule, with the proviso that when X is methylene, $A^4$ cannot be a hydrogen atom or a nitro group; and $R^1$, $R^2$, $R^3$, and $R^4$ independently represent a hydrogen atom, an amino group, a nitro group or a thiocyanato group.

The term "a biocompatible molecule" as used herein means a molecule that is compatible with targeted cells or tissues, i.e., the molecule is biologically active to bind the targeted cells or tissues. Preferably, the biocompatible molecule is a peptide sequence, an antibody, etc. As a blood pool contrast agent, the biocompatible molecule should be able to couple to the human serum albumin (HSA), while as a targeting contrast agent, the molecule should be able to couple to the targeted cell or organs.

When $A^4$ of Formula (I) is selected from a hydrogen atom, a nitro group, an amino group or a thiocyanato group, the metal complex containing the ligand of Formula (I) is useful as a blood pool contrast agent. When $A^4$ of Formula (I) is —Z—Y, the metal complex containing the ligand of Formula (I) is useful as a targeting contrast agent.

Preferably, $A^4$ is a hydrogen atom or a thiocyanato group.

Preferably, $A^4$ is —Z—Y, Z is selected from

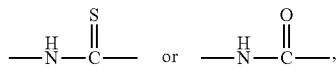

and Y is a group derived from a targeting peptide sequence. The "targeting peptide sequence" may be chosen or designed according to the target. More preferably, the targeting peptide sequence is selected from interleukin 11 (IL-11), bombesin (BN), cyclo(Arg-Gly-Asp) (cRGD) or Leu-Ala-Arg-Leu-Leu-Thr (D4).

Preferably, X is methylene or 1,1-cyclobutylene.

Preferably, $A^1$, $A^2$ and $A^3$ independently represent a hydrogen atom, methyl, benzyl, methoxybenzyl, diphenyl methyl, or isothiocyanatobenzyl. $A^1$, $A^2$ and $A^3$ can be used to increase liposolubility of the ligand, and be chosen according to the actual requirements.

In a preferred embodiment of this invention, X is 1,1-cyclobutylene, and $A^1$, $A^2$, $A^3$, $A^4$, $R^1$, $R^2$, $R^3$ and $R^4$ independently represent a hydrogen atom. The preferred embodiment has a molecular structure shown below:

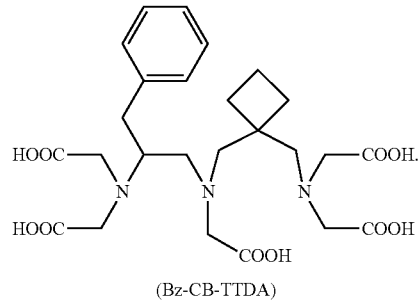 [SMILES: "(Bz-CB-TTDA)" ; O=C(O)CN(CC(=O)O)CC1(CN(CC(=O)O)CC(Cc2ccccc2)N(CC(=O)O)CC(=O)O)CCC1]

(Bz-CB-TTDA)

In another preferred embodiment of this invention, X is methylene, $A^4$ is a thiocyanato group, and $A^1$, $A^2$, $A^3$, $R^1$, $R^2$, $R^3$ and $R^4$ independently represent a hydrogen atom. The preferred embodiment has a molecular structure shown below:

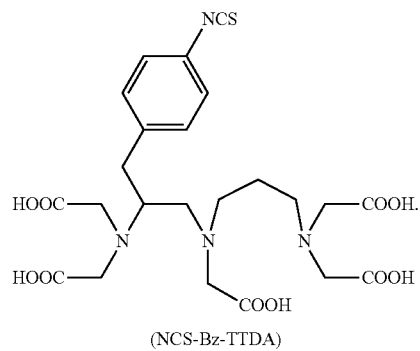

(NCS-Bz-TTDA)

In yet another preferred embodiment of this invention, X is methylene, $A^4$ is —Z—Y, Z is

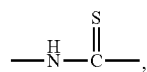

Y is a group derived from IL-11, and $A^1$, $A^2$, $A^3$, $R^1$, $R^2$, $R^3$ and $R^4$ independently represent a hydrogen atom. The preferred embodiment has a molecular structure shown below:

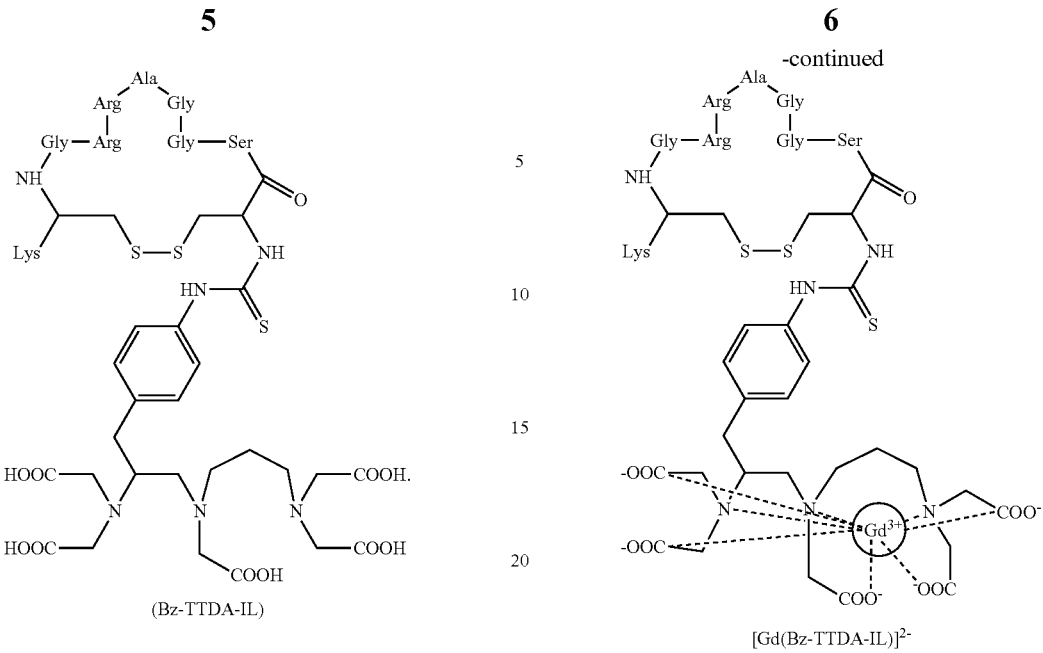

(Bz-TTDA-IL)

Preferably, the paramagnetic metal ion is selected from lanthanide series metal ions, $Mn^{2+}$, or $Fe^{3+}$. More preferably, the metal ion is selected from $Gd^{3+}$, $Mn^{2+}$, or $Fe^{3+}$. In a preferred embodiment of this invention, the metal ion is $Gd^{3+}$.

This invention provides a metal complex useful as a targeting contrast agent. The metal complex comprises a paramagnetic metal ion and a ligand of Formula (i) chelated with the paramagnetic metal ion:

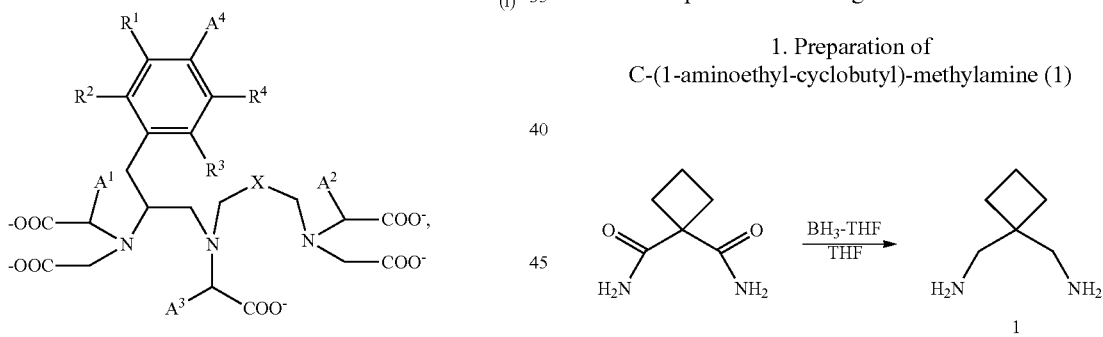

wherein, in Formula (i), X, $A^1$, $A^2$, $A^3$, $A^4$, $R^1$, $R^2$, $R^3$ and $R^4$ have the same definitions as in Formula (I).

Two preferred embodiments of the metal complex of this invention are shown below:

[Gd(Bz-CB-TTDA)]$^{2-}$

[Gd(Bz-TTDA-IL)]$^{2-}$

The following examples and comparative examples are provided to illustrate the merits of the preferred embodiments of the invention, and should not be construed as limiting the scope of the invention.

EXAMPLE

Example 1

Preparation of the Ligand: Bz-CB-TTDA

1. Preparation of C-(1-aminoethyl-cyclobutyl)-methylamine (1)

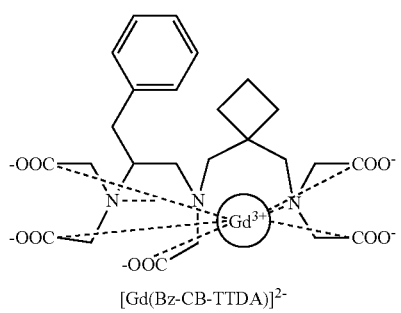

5.2 g (36.6 mol) of cyclobutane-1,1-dicarboxylic acid diamine, 250 mL of anhydrous THF and 300 mL of 1M $BH_3$-THF solution [$BH_3$:THF=1:8 (mol ratio)] were mixed in an ice bath under a nitrogen gas environment. The mixture was subjected to reaction in the ice bath for one hour and then to reflux reaction at 70° C. for 36 hours to obtain a reaction solution. Then, methanol was added into the reaction solution to terminate the reaction, followed by evaporation to obtain a crude product. The crude product was mixed with 250 mL of ethanol and 50 mL of 6N HCl solution. The mixture was then refluxed at 80° C. for 12 hours, followed by evaporation to obtain a yellow oil. The yellow oil was mixed with water and HCl solution to adjust pH to 2. The mixture was then purified by placing in a column (3×20 cm) filled with 100 mL of AG 50 W×8 cationic exchange resin (available from Aldrich Co., 200~400 mesh, $H^+$ type) and elutriating with HCl solutions having gradient concentrations from 0.5 N to 3.0 N, collecting an eluent fraction of gradient concentrations from 1.0 N to 2.0 N, and followed by evaporating the eluent fraction to obtain a product of g (26.3 mmol, 70.9%) of C-(1-aminoethyl-cyclo-butyl)-methylamine 1. The analytic data of the product are as follows: $^1$H-NMR (D$_2$O, 400 MHz) δ(ppm): 2.95 (s, 4H, NH$_2$CH$_2$CCH$_2$NH$_2$), 1.87-1.81 (m, 6H, CCH$_2$CH$_2$CH$_2$); $^{13}$C-NMR (D$_2$O, 100 MHz), δ(ppm):49.93, 49.81, 36.91, 27.73, 26.28, 14.46; ESI-MS (m/z):calcd. 114.19, found 114.76 [M+H]$^+$; Anal. Calcd (Found) for C$_6$H$_{14}$N$_2$.3HCl: C, 32.44 (32.23); H, 7.20 (7.66); N, 12.24 (12.53).

2. Preparation of L-phenylalanine methyl ester (2)

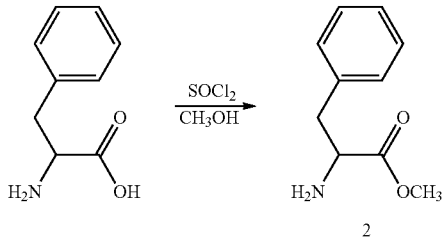

6.61 mL of SOCl$_2$ and 40 mL of methanol were thoroughly mixed in an ice bath for 30 minutes, followed by mixing with 10 g of L-phenylalanine. The mixture was subjected to a reflux reaction at 70° C. for 24 hours, followed by evaporating, re-crystallizing in ether, filtering and drying to obtain a product of 11.5 g (88.3%) of L-phenylalanine methyl ester 2. The analytic data of the product are as follows: $^1$H-NMR (D$_2$O, 400 MHz), δ(ppm): 7.36-7.20 (m, 5H, Ar), 4.36-4.34 (t, 1H, J=6, H$_2$NHCH), 3.75 (s, 3H, OCH$_3$), 3.30-3.12 (m, 2H, CH$_2$Ar); $^{13}$C-NMR (D$_2$O, 100 MHz), δ(ppm): 170.2, 133.9, 129.5, 129.4, 129.3, 128.3, 128.1, 54.2, 53.7, 35.7; ESI-MS (m/z): calcd. 179.22, found 180.13 [M+H]$^+$; Anal. Calcd (Found) for C$_{10}$H$_{13}$NO$_2$.HCl: C, 55.69 (55.32); H, 6.45 (6.54); N, 6.49 (6.35).

3. Preparation of 2-amino-N-((1-(aminomethyl)cy-clo-butyl)-methyl)-3-phenylpropanamide (3)

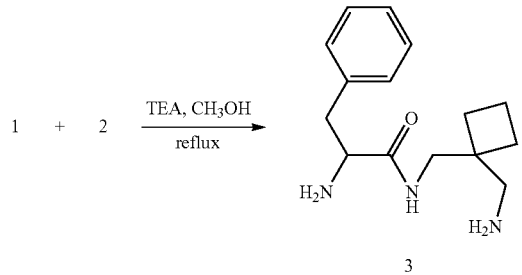 [SMILES: NCC1(CNC(=O)C(N)Cc2ccccc2)CCC1]

3.6 g (31.5 mmol) of 1 was mixed with 100 mL of methanol, followed by adding triethyl amine to adjust pH to 9-10 to obtain a first reaction solution. 5.1 g (28.7 mmol) of 2 was mixed with 100 mL of methanol to obtain a second reaction solution. The second reaction solution was added dropwisely into the first reaction solution to obtain a reaction mixture. The reaction mixture was subjected to reflux reaction at 60-70° C. for 19 hours, followed by evaporation to obtain a crude product. The crude product was dissolved in ammonia, followed by extracting with chloroform and water and evaporating to obtain a product of 2.9 g (11.1 mmol, 38.6%) of a light-yellow oil 3. The analytic data of the product are as follows: $^1$H-NMR (D$_2$O, 400 MHz), δ(ppm): 7.29-7.15 (m, 5H, Ar), 3.57 (t, 1H, J=3, H$_2$NCH), 3.20-2.95 (m, 2H, NHCH$_2$), 2.89-2.76 (m, 2H, CH$_2$Ar), 2.21-2.05 (m, CH$_2$NH$_2$), 1.69-1.66 (m, 2H, CH$_2$CH$_2$CH$_2$), 1.52-1.45 (m, 4H, CH$_2$CH$_2$CH$_2$); $^{13}$C-NMR (D$_2$O, 100 MHz), δ(ppm): 176.88, 137.37, 129.38, 128.90, 127.11, 56.60, 45.82, 43.99, 42.36, 40.90, 26.59, 26.51, 14.27; ESI-MS (m/z): calcd. 261.36, found 262.18 [M+H]$^+$; Anal. Calcd (Found) for C$_{15}$H$_{23}$N$_3$O.HCl: C, 60.94 (60.49); H, 8.43 (8.12); N, 14.53 (14.11).

4. preparation of (4-benzyl-8-cyclobutyl-3,6,10-tri-(carboxymethyl)-3,6,10-triazadodecanedioic acid (Bz-CB-TTDA)

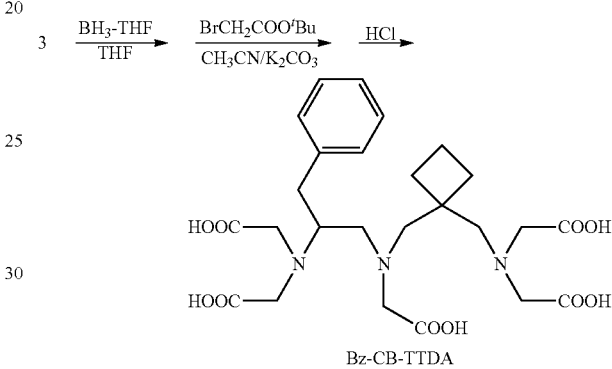

Bz-CB-TTDA 36.7 mL of 1M BH$_3$-THF solution [BH$_3$:THF=1:4 (mole ratio)] was added dropwisely into 2.4 g (9.2 mmol) of 3 to obtain a reaction solution. The reaction solution was subjected to reaction in an ice bath for 1 hour and then to reaction at 70° C. for 36 hours. 50 mL of ethanol and 10 mL of 6N HCl solution were added into the reaction solution, followed by subjecting the reaction solution to reflux reaction at 80° C. for 12 hours and evaporating to obtain a matter. The matter was dissolved in ammonia, followed by extracting with chloroform and water, and evaporating to obtain a product of 1.9 g (7.7 mmol, 38.6%) of yellow oil.

The yellow oil was dissolved into 250 mL of CH$_3$CN to obtain a solution and was mixed with 8.0 g (57.8 mmol) of K$_2$CO$_3$ to adjust pH to 10, followed by mixing with 6.1 mL (42.4 mmol) of BrCH$_2$COO$^t$Bu to obtain a reaction solution. The reaction solution was subjected to reflux reaction at 70° C. for 48 hours, followed by filtering, evaporating, extracting with chloroform and water, re-evaporating, and mixing with 100 mL of 3N HCl solution to obtain a mixing solution. The mixing solution was subjected to reaction at room temperature for 24 hours, and then to evaporation to obtain a crude product. The crude product was dissolved in water, and was mixed with ammonia to adjust pH to 11~12. The mixture was then purified by placing in a column (3×20 cm) filled with 100 mL of AG1×8 anionic exchange resin (available from Aldrich Co., 200~400 mesh, HCOOH type) and elutriating with formic acid solutions having gradient concentrations from 0.1 N to 3.0 N, collecting an eluent fraction of a concentration of 0.8 N, and followed by evaporating an eluent collected therefrom to obtain a product of 1.4 g (2.7 mmol, 34.8%) of Bz-CB-TTDA. The analytic data of the product are as follows: $^1$H-NMR (D$_2$O, 400 MHz), δ(ppm): 7.34-7.23 (m, 5H, Ar), 3.82-3.60 (s, 10H, CH$_2$COOH), 3.58-3.28 (m, 6H, ArCH$_2$CH$_2$NHCH$_2$), 3.16 (d, 2H, J=14, CH$_2$NH$_2$), 2.71 (m, 1H, H$_2$NCH), 1.87 (m, 6H, CCH$_2$CH$_2$CH$_2$); $^{13}$C-NMR (D$_2$O, 100 MHz), δ(ppm): 185.04, 136.48, 129.59, 129.30, 127.52, 62.05, 60.68, 60.27, 58.30, 57.36, 55.36, 54.41, 53.09, 39.39, 33.14, 30.14, 15.86; ESI-MS (m/z): calcd. 537.56, found 537.84 [M+H]$^+$; Anal. Calcd (Found) for $C_{25}H_{35}N_3O_{10}\cdot 3HCl\cdot 5H_2O$: C, 40.52 (40.74); H, 6.57 (6.56); N, 5.42 (5.70).

Example 2

Preparation of the Ligand Bz-TTDA-IL 1. preparation of p-Nitrophenylalanine methylester (NBPDA)

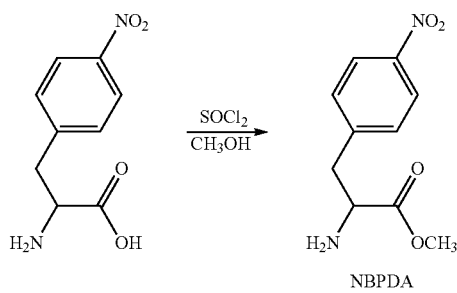

NBPDA 10 mL of $SOCl_2$ and 40 mL of methanol were thoroughly mixed in an ice bath for 30 minutes, followed by mixing with 0.51 g of p-nitrophenylalanine to obtain a reaction solution. The reaction solution was subjected to reflux reaction at 70° C. for 24 hours, followed by evaporating, re-crystallizing in ether, and filtering to obtain a product of 0.53 g (97.0%) of a white solid of NBPDA.

2. preparation of 2-Amino-N-(1-aminomethyl)-3-(4-nitro-phenyl)-propionamide (NP1)

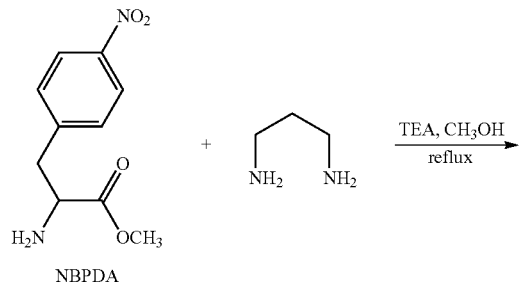

2.00 g (0.0175 mol) of (1-aminomethyl)methylamine and 50 mL of methanol were mixed to obtain a first reaction solution, the pH of which was adjusted to 9~10 by adding a proper amount of triethyl amine. 2.10 g (0.0093 mol) of NBPDA and 100 mL of methanol were mixed to obtain a second reaction solution. The second reaction solution was added dropwisely into the first reaction solution, followed by reacting for 12 hours and evaporating to obtain a yellow oil. The yellow oil was stirred in water and was mixed with HCl to adjust pH to 2 so as to obtain a crude product. The crude product was purified by placing in a column (3×20 cm) filled with 100 mL of AG 50 W×8 cationic exchange resin and elutriating with HCl solutions having gradient concentrations from 0.1 N to 4.0 N, collecting an eluent fraction of gradient concentrations from 2.5 N to 3.5 N, and followed by evaporating the eluent fraction to obtain a product of 1.43 g (0.019 mol, 40.4%) of NP1.

3. preparation of N1-(1-(aminomethyl)methyl)-3-(4-nitrophenyl)propane-1,2-diamine (NP2)

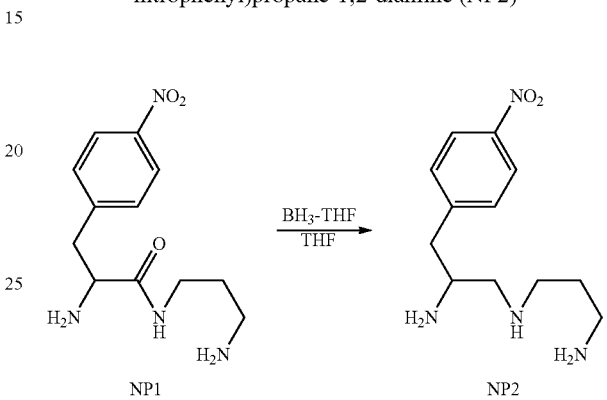

6.37 g (0.038 mol) of NP1, 50 mL of anhydrous THF, and 300 mL of 1 M $BH_3$-THF solution [$BH_3$:THF=1:8 (mole ratio)] were mixed in an ice bath under a nitrogen gas environment to obtain a reaction solution. The reaction solution was subjected to reaction in an ice bath for 1 hour, and then to reaction at 70° C. for 36 hours, followed by evaporation. The matter thus obtained was mixed with 100 mL of ethanol and 10 mL of 6N HCl, followed by reflux reaction for 12 hours and evaporating to obtain a yellow oil. The yellow oil was stirred in water and was mixed with HCl to adjust pH to 2 so as to obtain a crude product. The crude product was purified by placing in a column (3×20 cm) filled with 100 mL of AG 50 W×8 cationic exchange resin and elutriating with HCl solutions having gradient concentrations from 0.1 N to 5.0 N, collecting an eluent fraction of gradient concentrations from 3.5 N to 4.0 N, and followed by evaporating the eluent fraction to obtain a product of 2.98 g (0.019 mol, 50.0%) of NP2.

4. preparation of 4-(4-nitrobenzyl)-3,6,10-tri-(carboxymethyl)-3,6,10-triazadodecanedioic acid ($NO_2$-Bz-TTDA)

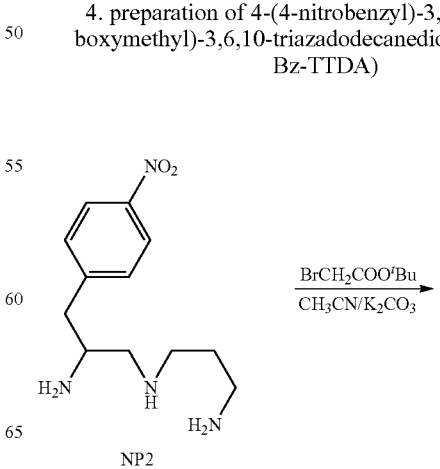

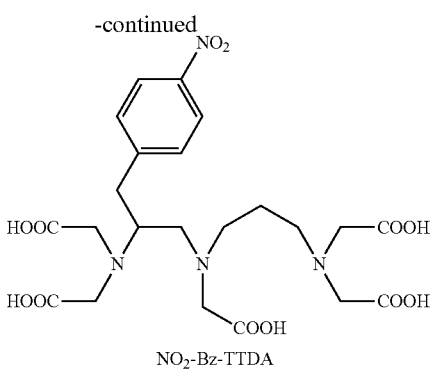

NO₂-Bz-TTDA 2.98 g (0.019 mol) of NP2 was dissolved into 250 mL of CH₃CN, followed by mixing with 10 g of K₂CO₃ to adjust pH to 10 and with 21.19 mL (0.143 mol) of BrCH₂COO$^t$Bu to form a reaction solution. The reaction solution was refluxed for 48 hours, followed by filtering and evaporating to obtain a crude product. The crude product was extracted with chloroform and water, followed by evaporation and purification using silica column chromatography (eluent: CH₂Cl₂/CH₃OH=19/1) to obtain a product of 4.92 g (6.18 mmol, 35.4%) of NO₂-Bz-TTDA.

5. preparation of 4-(4-aminobenzyl)3,6,10-tri-(carboxymethyl)-3,6,10-triazadodecanedioic acid (NH₂-Bz-TTDA)

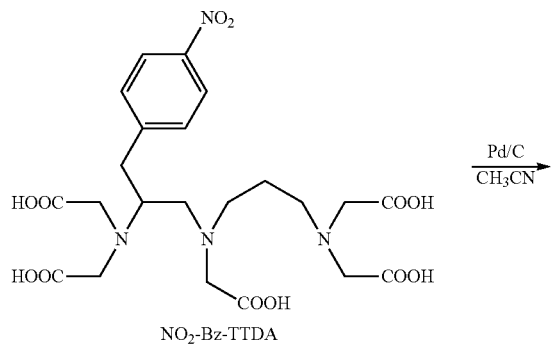

1.03 g (1.25 mmol) of NO₂-Bz-TTDA was dissolved into 50 mL of CH₃CN, and was mixed with 24.8 mg of Pd/C to form a reaction solution. The reaction solution was charged into a reactor. The reactor was vacuumed for 3 minutes, followed by introducing H₂ therein to adjust the pressure to 1.5 kg/cm², allowing reaction to take place by stirring at room temperature for 4 hours, and evaporating when the pressure in the reactor was kept constant to form a crude product. The crude product was purified using silica column chromatography (eluent: CH₂Cl₂/CH₃OH=19/1) so as to obtain a product of 0.82 g (1.03 mmol, 82.4%) of NH₂-Bz-TTDA.

6. preparation of 4-(4-thiocyanatobenzyl)-3,6,10-tri-(carboxymethyl)-3,6,10-triazadodecanedioic acid (NCS-Bz-TTDA)

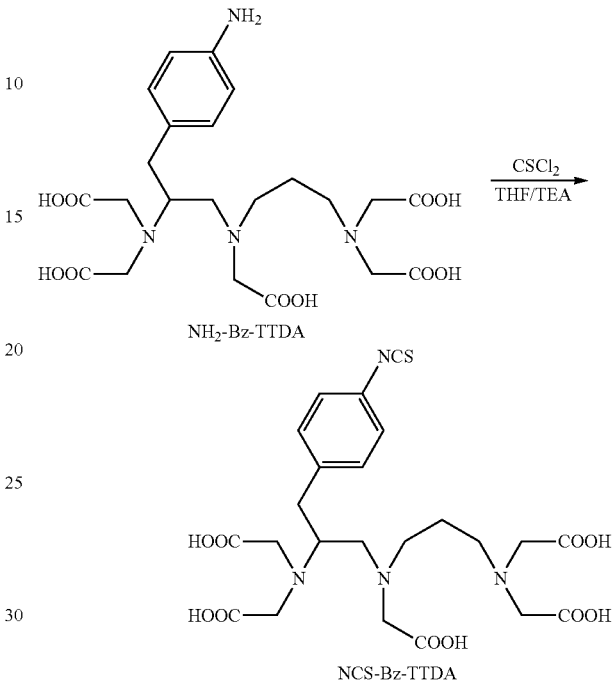

1.9 mL (3.09 mmol) of CSCl₂, 0.82 g (1.03 mmol) of NH₂-Bz-TTDA, 40 mL of THF and 2 mL of triethylamine were mixed to form a reaction solution. The reaction solution was subjected to reaction under a nitrogen gas environment for 12 hours, followed by evaporation to obtain a crude product. The crude product was purified using silica column chromatography (eluent: CH₂Cl₂/methanol=19/1) so as to obtain 0.72 g (3.05 mmol, 83.7%) of yellow oil of NCS-Bz-TTDA.

7. Bz-TTDA-IL (1) Preparation of Resin Containing IL-11

156 mg (0.1 mmol) of resin (available from Kelowna International Scientific Inc., R.O.C., the resin was a type of rink amide) and 5 mL of dimethylformamide (DMF) were thoroughly mixed in a reactor for 30 minutes. After the resin swelled, DMF was removed from the reactor.

[De-protection]: 10 mL of piperidine-DMF mixing solution (volume ratio: 20%) was added into the reactor to proceed with de-protective reaction for 10 minutes. The above step was repeated. The resin thus treated was sampled for Kaiser test in order to determine whether the de-protective reaction was complete.

[Preparing amino acid]: 0.4 mmol of an amino acid specified in the amino acid sequence of IL-11, 208 mg (0.4 mmol) of benzotriazole-1-yl-oxy-tris-pyrrolidino-phosphonium-hexafluorophosphate (PyBOP), and 3 mL of an activator (0.4 M of N-methylmorpholine (NMM)-DMF mixing solution) were thoroughly mixed at room temperature for 10 minutes to obtain a mixture.

[bonding amino acid]: The mixture was added into the aforesaid reactor and subjected to react with the resin for 4-6 hours, followed by washing the resin in the reactor. The resin was sampled for Kaiser test in order to determine whether the bonding of amino acid with the resin was complete.

The above steps, [De-protection], [Preparing amino acid] and [bonding amino acid] were repeated until the desired amino acid sequence of IL-11 was obtained, and thereby the resin containing IL-11 was obtained.

(2) Preparation of Bz-TTDA-IL 0.72 g (0.862 mmol) of NCS-Bz-TTDA and 0.5 g (0.31 mmol) of the resin containing IL-11 were placed in a PS3 reactor, followed by adding 10 mL of DMSO and 5 mL of N-diisopropylethylamine (DIPEA) into the PS3 reactor, and allowing reaction to take place at 25° C. for 24 hours to obtain the modified resin. 0.5 g of the modified resin thus obtained and 10 mL of a de-protective agent of a mixture of trifluoroacetic acid, deionized water, ethanedithiol and triisopropylsilane (TIS) in a volume ratio of 94.5/2.5/2.5/1 were mixed under stirring for 1.5 hours, followed by washing the resin with methanol and toluene, filtering and collecting the filtrate, adding triethylamine into the filtrate so as to neutralize the residual trifluoroacetic acid, evaporating to remove the solvent, adding dropwisely an ice ether into the filtrate in an ice bath, centrifuging with a rotating rate of 1500 rpm for 5 minutes, washing the filtrate with ether till an upper layer became transparent, and taking the upper layer out of the filtrate. Deionized water was added into the upper layer, followed by freezing in a refrigerator so as to obtain a red powder. The red powder was dried to form a crude product, followed by purifying using HPLC to obtain Bz-TTDA-IL.

Example 3

Preparation of Metal Complex [Gd(Bz-CB-TTDA)]$^{2-}$ 0.2 mmol of ligand Bz-CB-TTDA prepared in Example 1 and 0.25 mmol of GdCl$_3$ were mixed, followed by adding 5 mL of deionized water to form a reaction solution. The reaction solution was refluxed for 24 hours, followed by adjusting pH to 8, precipitating, neutralizing, filtering and drying so as to prepare a crystal of metal complex [Gd(Bz-CB-TTDA)]$^{2-}$.

Example 4

Preparation of Metal Complex [Gd(Bz-TTDA-IL)]$^{2-}$

The procedures and conditions in preparing the metal complex of Example 4 were similar to those of Example 3, except that in Example 4, ligand Bz-TTDA-IL was used to replace Bz-CB-TTDA.

Comparative Example 1

Preparation of ligand 8-cyclobutyl-3,6,10-tri-(carboxymethyl)-3,6,10-triazadodecanedioic acid (CB-TTDA)

1. preparation of 1-cyano-cyclobutylcarboxylic acid methyl ester (4)

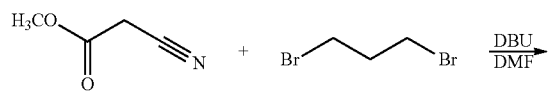

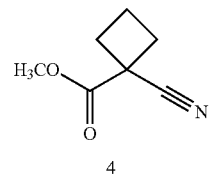

4

10 g (0.1 mol) of methyl cyanoacetate and 10 mL of anhydrous DMF were mixed under stirring for 10 minutes, followed by adding 33.4 g (0.22 mol) of 1,8-diazabicyclo[5,4,0]undec-7-ene (DBU) at 10-20° C. into the mixture, heating the mixture to 50° C. to allow reaction to take place for 15 minutes, moving the mixture to an ice bath (−5~−10° C.) of a mixture of liquid nitrogen and acetone, and adding 20.4 g (0.10 mol) of 1,3-dibromopropane dissolved in 10 mL of anhydrous DMF into the mixture to form a reaction solution. The reaction solution was subjected to reaction at 25° C. for 15 minutes, and to further reaction at 70° C. for 30 minutes, followed by evaporating, extracting with CH$_2$Cl$_2$ and deionized water, collecting an organic layer from the extraction, evaporating, purifying using silica column chromatography (eluent: acetone/hexane=8/1), and re-evaporating to obtain a product of 8.74 g (0.063 mol, 62.85%) of 4.

2. preparation of 1-cyano-cyclobutylcarboxylic acid (2-amino-ethyl)amide (5)

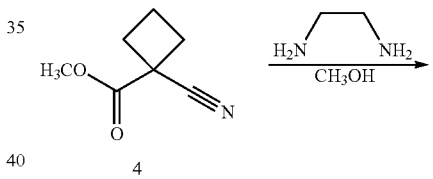

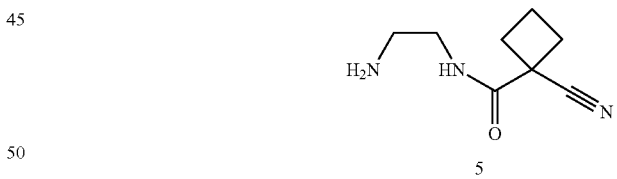

5

8.74 g (0.063 mol) of 4 and 50 mL of methanol were mixed, after which the mixture was added dropwisely into 3.77 g (4.25 mL) of ethylene diamine to form a reaction solution. The reaction solution was subjected to reaction at room temperature for 15 hours, followed by evaporation to obtain yellow oil. The yellow oil was stirred with water and was mixed with HCl to adjust pH to 2 to obtain a crude product. The crude product was purified by placing in a column (3×20 cm) filled with 100 mL of AG 50 W×8 cationic exchange resin and elutriating with water and HCl solution having gradient concentrations, collecting an eluent fraction of a gradient concentration from 0.5 N to 1.0 N, and followed by evaporating the eluent fraction to obtain 6.37 g (0.038 mol, 60.49%) of 5.

3. N'-((1-(aminomethyl)-cyclobutyl)methyl)ethane-1,
2-diamine (6)

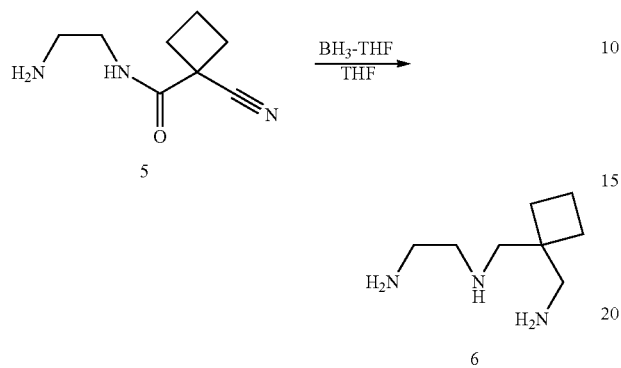

6.37 g (0.038 mol) of 5 and 50 mL of anhydrous THF were mixed, followed by adding 300 mL of 1 M BH$_3$-THF solution to the mixture in an ice bath (−10° C.) of liquid nitrogen and acetone under a nitrogen gas environment to form a reaction solution. The reaction solution was subjected to reaction at −5~0° C. for 1 hour, followed by heating the reaction solution to 70° C. to allow reaction to take place for 36 hours, and evaporating to obtain a solid substance. The solid substance, 100 mL of ethanol and 10 mL of 6N HCl were mixed, refluxed for 12 hours, followed by evaporation to form yellow oil. The yellow oil was stirred in water and was mixed with HCl to adjust pH to 2 to obtain a crude product. The crude product was purified by placing in a column (3×20 cm) filled with 100 mL of AG 50 W×8 cationic exchange resin and elutriating HCl solutions having gradient concentrations, collecting an eluent fraction of gradient concentration from 3.5 N to 4.0 N, and followed by evaporating the eluent fraction to obtain 2.98 g (0.019 mol, 50%) of 6.

4. CB-TTDA:

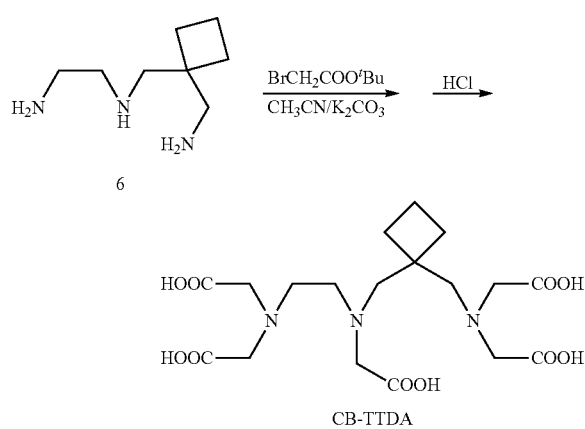

2.98 g (0.019 mol) of 6 was dissolved into 250 mL of CH$_3$CN, mixed with 10 g of K$_2$CO$_3$ to adjust pH to 10, and further mixed with 21.19 mL (0.143 mol) of BrCH$_2$COO$^t$Bu to form a reaction solution. The reaction solution was refluxed for 48 hours, followed by filtering to obtain a filtrate, evaporating and extracting the filtrate with chloroform and water, collecting the chloroform layer, re-evaporating, adding 100 mL of 3N HCl into the filtrate, allowing reaction to take place at room temperature for 24 hours, re-evaporating, and adjusting pH to 11.2 with ammonia to obtain a crude product. The crude product was purified by placing in a column (3×20 cm) filled with 100 mL of AG1×8 anionic exchange resin and elutriating with formic acid solutions having gradient concentrations from 0.1 N to 3.0 N, collecting an eluent fraction of a concentration of 1.2 N, and followed by evaporating the eluent fraction to obtain 2.72 g (0.006 mol, 31.98%) of CB-TTDA.

Comparative Example 2

Preparation of Metal Complex [Gd(CB-TTDA)]$^{2−}$

The procedures and conditions in preparing the metal complex of Comparative Example 2 were similar to those of Example 3, except that in Comparative Example 2, ligand CB-TTDA was used to replace Bz-CB-TTDA.

[Test]

1. Hydration number of the ligand Bz-CB-TTDA:

First, metal complexes of [Eu(Bz-CB-TTDA)]$^{2−}$ and [Eu(CB-TTDA)]$^{2−}$ were prepared in accordance with the procedures of Example 3 with GdCl$_3$ being replaced by EuCl$_3$.

Each of metal complexes [Eu(Bz-CB-TTDA)]$^{2−}$ and [Eu(CB-TTDA)]$^2$ was mixed with D$_2$O and H$_2$O to obtain two samples, respectively. The half-life τ of each sample was determined by a fluorescence spectrometer (available from Varian Co., model name: Cary-Eclipse), followed by calculating the hydration number (q) with the following two formulas (i) and (ii). The results thus obtained are listed in Table 1.

TABLE 1

| Metal complex | q in formula (i) | q in formula (ii) |
|---|---|---|
| [Eu(Bz-CB-TTDA)]$^{2−}$ | 1.26 ± 0.02 | 1.14 ± 0.03 |
| [Eu(CB-TTDA)]$^{2−}$ | 1.21 ± 0.01 | 1.09 ± 0.02 |

(i) q = A[1/τ$_{H_2O}$ − 1/τ$_{D_2O}$] A = 1.05
(ii) q = ([1/τ$_{H_2O}$ − 1/τ$_{D_2O}$] − 0.25) × 1.2

In Table 1, the hydration numbers of [Eu(Bz-CB-TTDA)]$^{2−}$ and [Eu(CB-TTDA)]$^{2−}$ are about 1, which indicates that the basic skeletons of Bz-CB-TTDA and CB-TTDA are the same as that of TTDA, i.e., metal complex [Gd(Bz-CB-TTDA)]$^{2+}$ prepared from the ligand Bz-CB-TTDA can be a stable eight-coordinate complex.

2. Relaxivity (γ$_1$) of the Metal Complex [Gd(Bz-CB-TTDA)]$^{2−}$:

The longitudinal relaxation time T$_1$ in each of different concentrations of [Gd(Bz-CB-TTDA)]$^{2−}$ was measured by a relaxometer (20 MHz) in a T$_1$ mode. The relaxivity of [Gd(Bz-CB-TTDA)]$^2$ is a slope determined by using a plot of "1/T$_1$" versus "concentration of [Gd(Bz-CB-TTDA)]$^{2−}$". The relaxivity of [Gd(CB-TTDA)]$^{2−}$ was also measured in accordance with the above step. The results thus obtained are listed in Table 2.

TABLE 2

| Metal complex | pH value | γ$_1$(mM$^{−1}$s$^{−1}$) |
|---|---|---|
| [Gd(Bz-CB-TTDA)]$^{2−}$ | 7.4 ± 0.1 | 4.29 ± 0.03 |
| [Gd(CB-TTDA)]$^{2−}$ | 7.4 ± 0.1 | 4.12 ± 0.05 |

TABLE 2-continued

| Metal complex | pH value | $\gamma_1 (mM^{-1}s^{-1})$ |
|---|---|---|
| [Gd(TTDA)]$^{2-}$ | 7.5 ± 0.1 | 3.85 ± 0.03[a] |
| [Gd(DTPA)]$^{2-}$ | 7.6 ± 0.1 | 3.89 ± 0.03[a] |

[a]The relaxivity of [Gd(TTDA)]$^{2-}$ is disclosed in *Inorg. Chem.*, 2005, 44, 382; The relaxivity of [Gd(DTPA)]$^{2-}$ is disclosed in *Am. J. Roentgenol.*, 1984, 142, 619-624.

In Table 2, the relaxivity of [Gd(Bz-CB-TTDA)]$^{2-}$ is higher than that of [Gd(CB-TTDA)]$^{2-}$ and [Gd(TTDA)]$^{2-}$, and also higher than that of the commercial [Gd(DTPA)]$^{2-}$. 3. Water exchange rate ($k_{ex}$) and molecular rotational correlation time ($\tau_R$) of [Gd(Bz-CB-TTDA)]$^{2-}$:

According to the disclosure of *Chem. Rev.*, 1999, 99, 2293-2352, the relaxivity of the metal complex is affected by the hydration number q and the correlation time $\tau_c$. The correlation time $\tau_c$ depends on three parameters: (1) molecular rotational correlation time ($\tau_R$); (2) Electron longitudinal and transverse spin relaxation time ($T_{1e}$, $T_{2e}$); and (3) Water residence lifetime ($\tau_m$) or Water exchange rate ($k_{ex}$), $\tau_m^{-1}=k_{ex}$. Since Bz-CB-TTDA and CB-TTDA have the same hydration number, comparison between Bz-CB-TTDA and CB-TTDA in relaxivity can be determined by the aforesaid parameters, i.e., the higher the parameters, the higher will be the relaxivity.

Electron longitudinal and transverse spin relaxation time ($T_{1e}$, $T_{2e}$) of each test sample of the metal complexes was measured by using $^{17}$O-NMR in a magnetic field of 9.4 T. The water exchange rate at 298 K ($K_{ex}^{298}$) and the molecular rotational correlation time at 298 K ($\tau_R^{298}$) of each test sample were determined by using three plots of "$T_1$ versus temperature", "$T_2$ versus temperature" and "chemical shift versus temperature". The results thus obtained are listed in Table 3.

TABLE 3

| | $k_{ex}^{298}$ ($10^6 s^{-1}$) | $\tau_R^{298}$ (ps) |
|---|---|---|
| [Gd(Bz-CB-TTDA)]$^{2-}$ | 271 ± 3.0 | 151 ± 3.0 |
| [Gd(CB-TTDA)]$^{2-}$ | 232 ± 4.0 | 112 ± 2.0 |
| [Gd(TTDA)]$^{2-}$ | 146 ± 17.0 | 104 ± 12.0 |
| [Gd(DTPA)]$^{2-}$ | 4.1 | 103 |

In Table 3, $k_{ex}^{298}$ and $\tau R^{298}$ of [Gd(Bz-CB-TTDA)]$^{2-}$ are higher than those of [Gd(CB-TTDA)]$^{2-}$, [Gd(TTDA)]$^{2-}$ and [Gd(DTPA)]$^{2-}$, which indicates that the relaxivity of [Gd(Bz-CB-TTDA)]$^{2-}$ is higher than those of [Gd (CB-TTDA)]$^{2-}$, [Gd (TTDA)]$^{2-}$ and [Gd (DTPA)]$^{2-}$.

4. Bound Relaxivity ($\gamma_1^b$):

Bound relaxivity ($\gamma_1^b$) between [Gd (Bz-CB-TTDA)]$^{2-}$ and HSA, and $\gamma_1^b$ between [Gd (CB-TTDA)]$^{2-}$ and HSA were measured by proton relaxation enhancement (PRE) method. The results thus obtained are listed in Table 4, and the structures of the commercial products [Gd(BOPTA)]$^{2-}$, MS-325 and [Gd(S)-EOB-DTPA]$^{2-}$ are shown below.

TABLE 4

| Metal complex | $\gamma_1^b (mM^{-1}s^{-1})$ |
|---|---|
| [Gd(Bz-CB-TTDA)]$^{2-}$ | 66.7 ± 2.2 |
| [Gd(CB-TTDA)]$^{2-}$ | 29.3 ± 0.8 |
| [Gd(BOPTA)]$^{2-}$ | 33.0[a] |

TABLE 4-continued

| Metal complex | $\gamma_1^b (mM^{-1}s^{-1})$ |
|---|---|
| MS-325 | 47.0 ± 4.0[a] |
| [Gd(S)-EOB-DTPA]$^{2-}$ | 44.1[a] |

[a]The $\gamma_1^b$ of [Gd(BOPTA)]$^{2-}$ is disclosed in Inorg. Chem., 1995, 34, 633-642; the $\gamma_1^b$ of MS-325 is disclosed in *J. Biol. Inorg. Chem.*, 1999, 4, 766-774; and the $\gamma_1^b$ of [Gd(S)-EOB-DTPA]$^{2-}$ is disclosed in *J. Biol. Inorg. Chem.*, 2001, 6, 196-200.

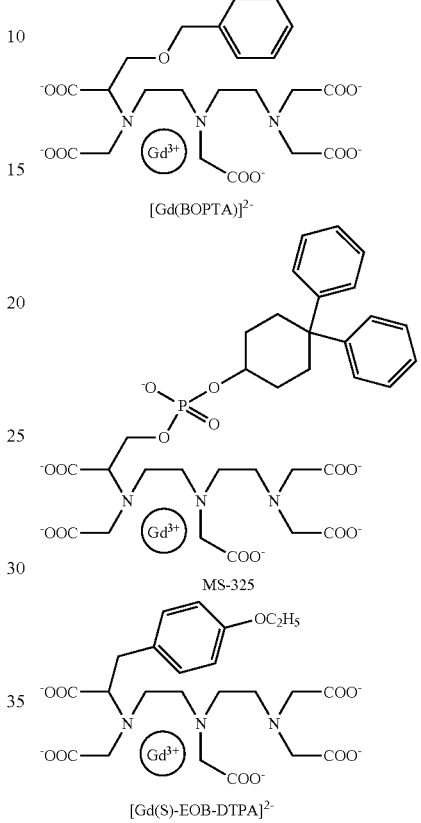

In Table 4, [Gd(Bz-CB-TTDA)]$^{2-}$ exhibits a bound relaxivity much higher than those of other metal complexes attributed to a higher water exchange rate and a good liposolubility.

5. Kinetic Stability of [Gd (Bz-CB-TTDA)]$^{2-}$:

Kinetic stability is evaluated by testing the stability of the metal complex in an environment containing a poisonous metal ion $Zn^{2+}$. The stability is defined as $R_1^P(t)/R_{1p}(0)$, in which $R_1^P(t)=1/T_1(t)$, $T_1$ is the relaxivity. The higher the $R_1^P(t)/R_{1p}(0)$, the higher will be the stability.

2.5 mM of each of [Gd(Bz-CB-TTDA)]$^{2--}$, [Gd(CB-TTDA)]$^{2-}$ and [Gd(DTPA)]$^{2-}$ was placed in a phosphate buffer saline (PBS, pH=7.4), followed by adding 2.5 mM of $ZnCl_2$ to obtain a sample. The sample was subjected to reaction at 37±0.1° C. for three days (t=3), after which the relaxivity $T_1(t)$ of the sample was determined by using NMR (20 MHz). The results thus obtained are listed in Table 5.

TABLE 5

| Metal complex | $R_1^P(t)/R_1^P(0)$ |
|---|---|
| [Gd(Bz-CB-TTDA)]$^{2-}$ | 46.14 |
| [Gd(CB-TTDA)]$^{2-}$ | 47.4 |
| [Gd(DTPA)]$^{2-}$ | 49.79 |

In Table 5, the stability of [Gd(Bz-CB-TTDA)]$^{2-}$ is comparable to those of [Gd(CB-TTDA)]$^2$ and [Gd(DTPA)]$^{2-}$ so as to prove that [Gd(Bz-CB-TTDA)]$^{2-}$ exhibits a better kinetic stability.

6. In vivo Image Study of [Gd(Bz-CB-TTDA)]$^2$:

10 μmol/kg of each of [Gd(Bz-CB-TTDA)]$^{2-}$ and a commercial product Magnevist was injected into two rats (available from the foundation of National Laboratory Animal Center, R.O.C.), followed by subjecting each of the rats to a measurement using a whole body MR scanner (3.0 T, condition: T1 dynamic pulse sequence, TR/TE=800/12). The images thus obtained are shown in FIG. 1 [(A) is the image from the rat injected with [Gd(Bz-CB-TTDA)]$^{2-}$ and (a) is the image from the rat injected with Magnevist].

In FIG. 1, the signal intensity of the image from [Gd(Bz-CB-TTDA)]$^{2-}$ is similar to that of Magnevist, which proves that [Gd(Bz-CB-TTDA)]$^{2-}$ can be used as a blood pool contrast agent.

7. In Vitro Image Study of [Gd(BZ-CB-TTDA)]$^{2-}$:

For each combination of the concentration and cell number in Table 6, [Gd(Bz-CB-TTDA)]$^{2-}$ and/or a positive cell line (HT-1080, which exhibits a low expression to IL-11Rα and is available from Bioresource Collection and Research Center (BCRC), R.O.C.) and a negative cell line (MDA-MB-231, which exhibits a high expression to IL-11Rα and is available from BCRC) were mixed, followed by culturing at 37±0.1° C. for 1 hour, and washing with PBS three times to obtain samples A-D. Samples A-D were subjected to a measurement using a T1-weighted image of MR scanner. The results thus obtained are listed in Table 6.

TABLE 6

|  | A | B | C | D |
|---|---|---|---|---|
| Conc. of [Gd(Bz-TTDA-IL)]$^{2-}$ (mM) | — | 1.0 | — | 1.0 |
| Cell number of positive cell line | 10$^6$ | 10$^6$ | — | — |
| Cell number of negative cell line | — | — | 10$^6$ | 10$^6$ |
| Signal intensity | 285 ± 1 | 496 ± 3 | 273 ± 2 | 299 ± 1 |

In Table 6, the signal intensity of sample B is higher than that of sample A, and the signal intensity of sample D is higher than that of sample C, which indicates that the sample with [Gd(Bz-TTDA-IL)]$^{2-}$ has a higher signal intensity than the sample without [Gd(Bz-TTDA-IL)]$^{2-}$. Moreover, the results show a synergistic effect on the signal intensity when the sample contains [Gd(Bz-TTDA-IL)]$^2$ and the positive cell line.

In conclusion, the metal complex of this invention exhibits a better relaxivity and a better bound relaxivity for MRI diagnosis, and is useful as a blood pool contrast agent or a targeting contrast agent.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

---

---

What is claimed is:

1. A metal complex, comprising:
   a paramagnetic metal ion; and
   a ligand of Formula (i) chelated with said paramagnetic metal ion:

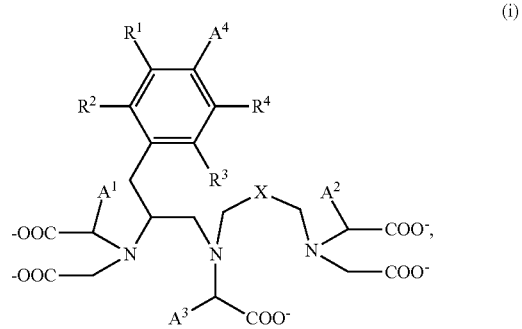

(i)

wherein, in Formula (i),

X represents methylene, 1,1-cyclobutylene, 1,1-cyclopentylene, or 1,1-cyclohexylene;

A$^1$, A$^2$ and A$^3$ independently represent a hydrogen atom, a C$_1$~C$_3$ alkyl group, a C$_1$~C$_3$ phenylalkyl group, a C$_1$~C$_3$ methoxyphenylalkyl group, diphenylmethyl or a C$_1$~C$_3$ isothiocyanato phenylalkyl;

A$^4$ represents a hydrogen atom, a nitro group, an amino group, a thiocyanato group, or —Z—Y, in which Z is a divalent linking group and Y is a biocompatible molecule, with the proviso that when X is methylene, A$^4$ cannot be a hydrogen atom or a nitro group; and R$^1$, R$^2$, R$^3$, and R$^4$ independently represent a hydrogen atom, an amino group, a nitro group or a thiocyanato group.

2. The metal complex of claim 1, wherein said metal ion is selected from lanthanide series metal ion, $Mn^{2+}$, or $Fe^{3+}$.

3. The metal complex of claim 2, wherein said lanthanide series metal ion is $Gd^{3+}$.

4. The metal complex of claim 1, wherein $A^4$ in Formula (i) is —Z—Y, Z is

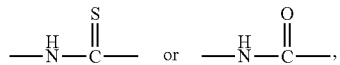

and Y is a targeting peptide sequence.

5. The metal complex of claim 4, wherein said targeting peptide sequence is selected from the group consisting of interleukin-11, bombesin, cyclo(Arg-Gly-Asp), and Leu-Ala-Arg-Leu-Leu-Thr.

6. The metal complex of claim 5, wherein X is methylene, $A^1$, $A^2$ and $A^3$ independently represent a hydrogen atom, and $R^1$, $R^2$, $R^3$ and $R^4$ independently represent a hydrogen atom.

7. The metal complex of claim 1, wherein X is methylene or 1,1-cyclobutylene.

8. The metal complex of claim 1, wherein $A^1$, $A^2$ and $A^3$ independently represent a hydrogen atom, methyl, benzyl, methoxyphenylmethyl, diphenylmethyl or isothiocyanato phenylmethyl.

9. The metal complex of claim 1, wherein X is methylene, $A^1$, $A^2$ and $A^3$ independently represent a hydrogen atom, $A^4$ is a thiocyanato group, and $R^1$, $R^2$, $R^3$ and $R^4$ independently represent a hydrogen atom.

10. The metal complex of claim 1, wherein X is 1,1-cyclobutylene, $A^1$, $A^2$, $A^3$ and $A^4$ independently represent a hydrogen atom, and $R^1$, $R^2$, $R^3$ and $R^4$ independently represent a hydrogen atom.

11. A ligand of Formula (I):

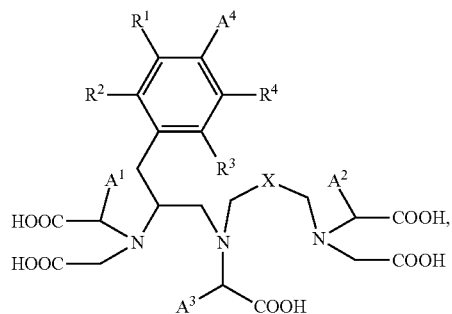

wherein, in Formula (I),

X represents methylene, 1,1-cyclobutylene, 1,1-cyclopentylene, or 1,1-cyclohexylene;

$A^1$, $A^2$ and $A^3$ independently represent a hydrogen atom, a $C_1$~$C_3$ alkyl group, a $C_1$~$C_3$ phenylalkyl group, a $C_1$~$C_3$ methoxyphenylalkyl group, diphenylmethyl or a $C_1$~$C_3$ isothiocyanato phenylalkyl;

$A^4$ represents a hydrogen atom, a nitro group, an amino group, a thiocyanato group, or —Z—Y, in which Z is a divalent linking group and Y is a biocompatible molecule, with the proviso that when X is methylene, $A^4$ cannot be a hydrogen atom or a nitro group; and $R^1$, $R^2$, $R^3$, and $R^4$ independently represent a hydrogen atom, an amino group, a nitro group or a thiocyanato group.

12. The ligand of claim 1, wherein $A^4$ is —Z—Y, Z is

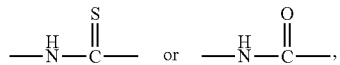

and Y is a targeting peptide sequence.

13. The ligand of claim 12, wherein said targeting peptide sequence is selected from the group consisting of interleukin-11, bombesin, cyclo(Arg-Gly-Asp), and Leu-Ala-Arg-Leu-Leu-Thr.

14. The ligand of claim 13, wherein X is methylene, $A^1$, $A^2$ and $A^3$ independently represent a hydrogen atom, and $R^1$, $R^2$, $R^3$ and $R^4$ independently represent a hydrogen atom.

15. The ligand of claim 11, wherein X is methylene or 1,1-cyclobutylene.

16. The ligand of claim 11, wherein $A^1$, $A^2$ and $A^3$ independently represent a hydrogen atom, methyl, benzyl, methoxyphenylmethyl, diphenylmethyl or isothiocyanato phenylmethyl.

17. The ligand of claim 11, wherein X is methylene, $A^1$, $A^2$ and $A^3$ independently represent a hydrogen atom, $A^4$ is a thiocyanato group, and $R^1$, $R^2$, $R^3$ and $R^4$ independently represent a hydrogen atom.

18. The ligand of claim 11, wherein X is 1,1-cyclobutylene, $A^1$, $A^2$, $A^3$ and $A^4$ independently represent a hydrogen atom, and $R^1$, $R^2$, $R^3$ and $R^4$ independently represent a hydrogen atom.

* * * * *